US00PP20789P2

(12) United States Plant Patent
Giesen

(10) Patent No.: US PP20,789 P2
(45) Date of Patent: Feb. 23, 2010

(54) *LOBELIA* PLANT NAMED 'TECH ELEBULE'
(50) Latin Name: *Lobelia erinus*
Varietal Denomination: Tech Elebule

(75) Inventor: Eric Giesen, Andijk (NL)
(73) Assignee: Goldsmith Seeds Europe B.V., Andijk (NL)

( * ) Notice: Subject to any disclaimer, the term of this patent is extended or adjusted under 35 U.S.C. 154(b) by 0 days.
(21) Appl. No.: 12/284,656
(22) Filed: Sep. 24, 2008
(51) Int. Cl.
*A01H 5/00* (2006.01)
(52) U.S. Cl. ..... Plt./451
(58) Field of Classification Search ..... Plt./451
See application file for complete search history.

*Primary Examiner*—June Hwu
(74) *Attorney, Agent, or Firm*—S. Matthew Edwards

(57) ABSTRACT

A new *Lobelia* plant named 'Tech Elebule,' particularly distinguished by bright blue, medium sized flowers, medium green foliage, spatulate leaves, freely branched, dense habit with short to medium internodes, initially spreading, then over hanging and trailing habit.

2 Drawing Sheets

Latin name of the genus and species of the plant claimed: *Lobelia erinus.*

Varietal denomination: 'Tech Elebule'.

BACKGROUND OF THE NEW PLANT

The present invention comprises a new and distinct cultivar of *Lobelia,* botanically known as *Lobelia erinus* and hereinafter referred to by the cultivar name 'Tech Elebule.'

'Tech Elebule' is a product of a planned breeding program. The new cultivar originated from a hybridization made in January 2004 in Andijk, Netherlands.

The female parent was an unpatented proprietary *Lobelia* plant designated 'LOB04-296-1,' having a white flower color. The male parent of 'Tech Elebule' was an unpatented proprietary *Lobelia* plant designated 'LOB04-288-1,' having a light blue flower color. 'LOB04-288-1' has darker foliage, smaller flowers, and is more pubescent than 'Tech Elebule.'

The resulting seeds were sown in March 2004 and 'Tech Elebule' was selected as one flowering plant within the progeny of the stated cross in July 2004 in a controlled environment in Andijk, Netherlands.

The first act of asexual reproduction of 'Tech Elebule' was accomplished when vegetative cuttings were propagated from the initial selection in the fall of 2004 in a controlled environment in Andijk, Netherlands.

Horticultural examination of plants grown from cuttings of the plant initiated in the spring of 2005 in Andijk, Netherlands, and in Hillscheid, Germany, and continuing thereafter, has demonstrated that the combination of characteristics as herein disclosed for 'Tech Elebule' are firmly fixed and are retained through successive generations of asexual reproduction. 'Tech Elebule' has not been observed under all possible environmental conditions. The phenotype may vary significantly with variations in environment such as temperature, light intensity and day length.

A Plant Breeders' Right for this cultivar was applied for with the European Union on Sep. 13, 2007. 'Tech Elebule' has not been made publicly available more than one year prior to the filing of this application.

DESCRIPTION OF THE DRAWINGS

This new *Lobelia* plant is illustrated by the accompanying photographs.

Figure 1:
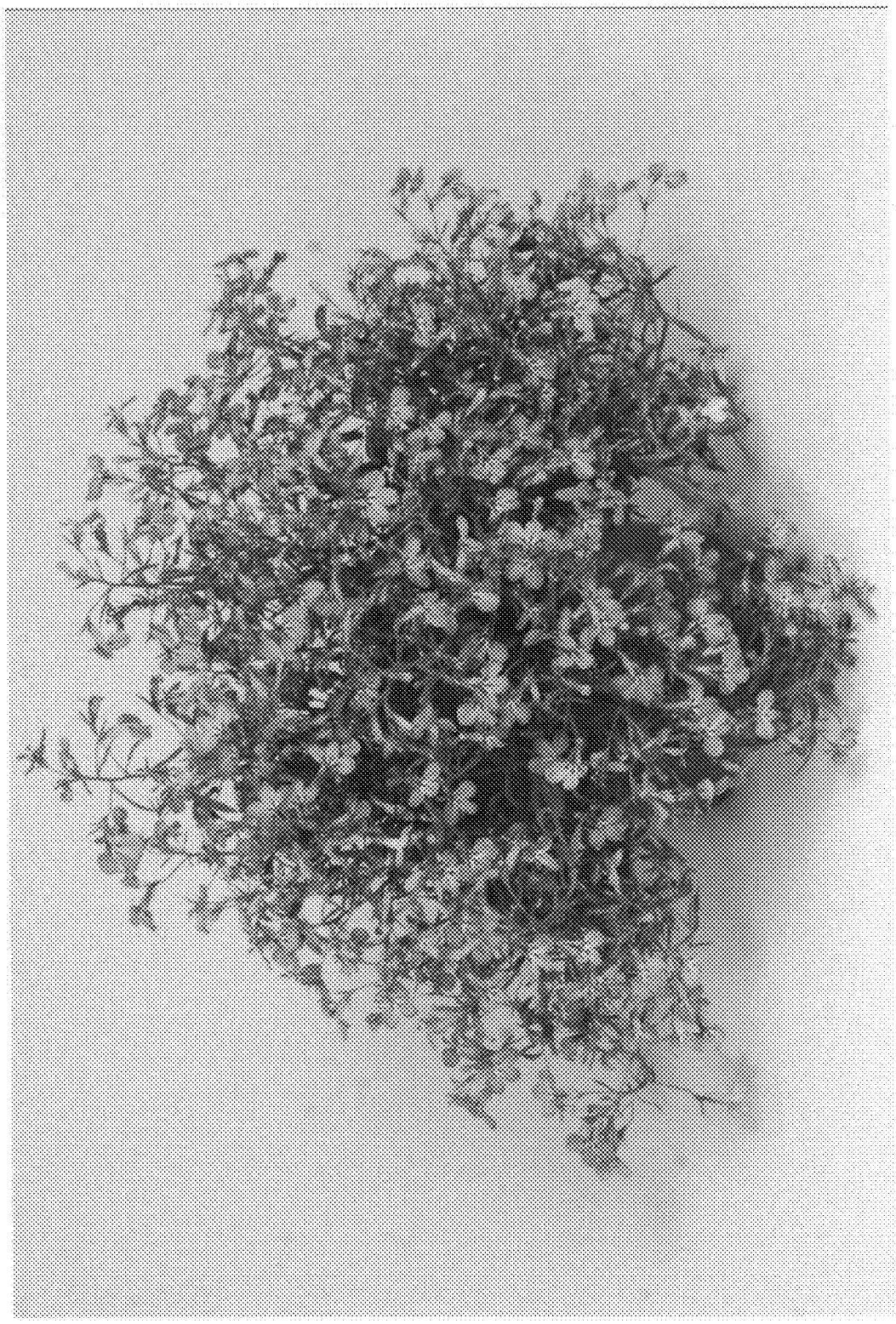
FIG. 1 shows a 17 week old greenhouse grown plant with flowers, buds, and foliage of the plant in full color.
Figure 2:
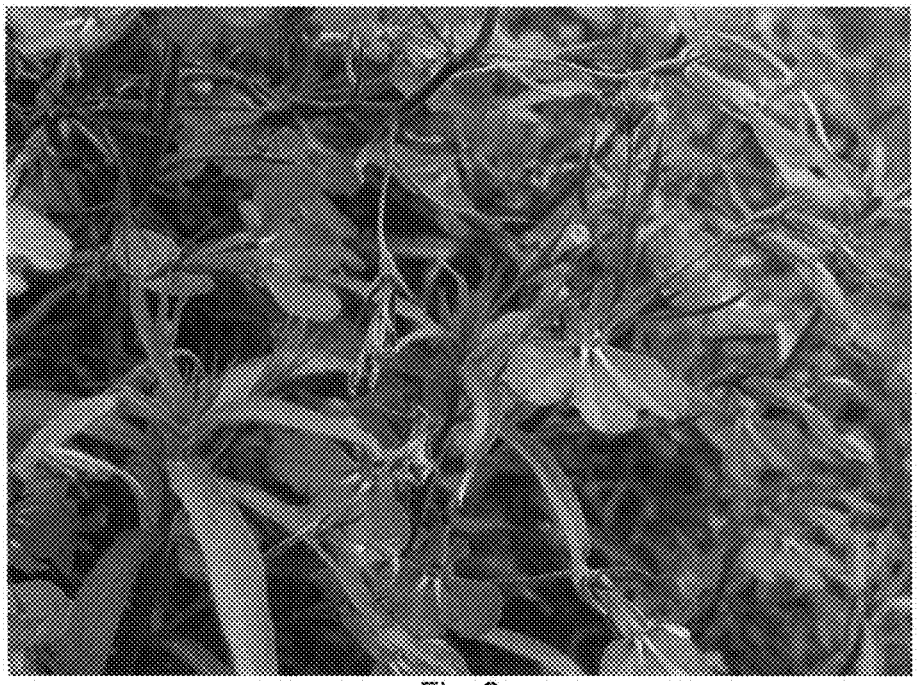
FIG. 2 shows a close view of the plant surface with shoot tips and flowers.
Figure 3:
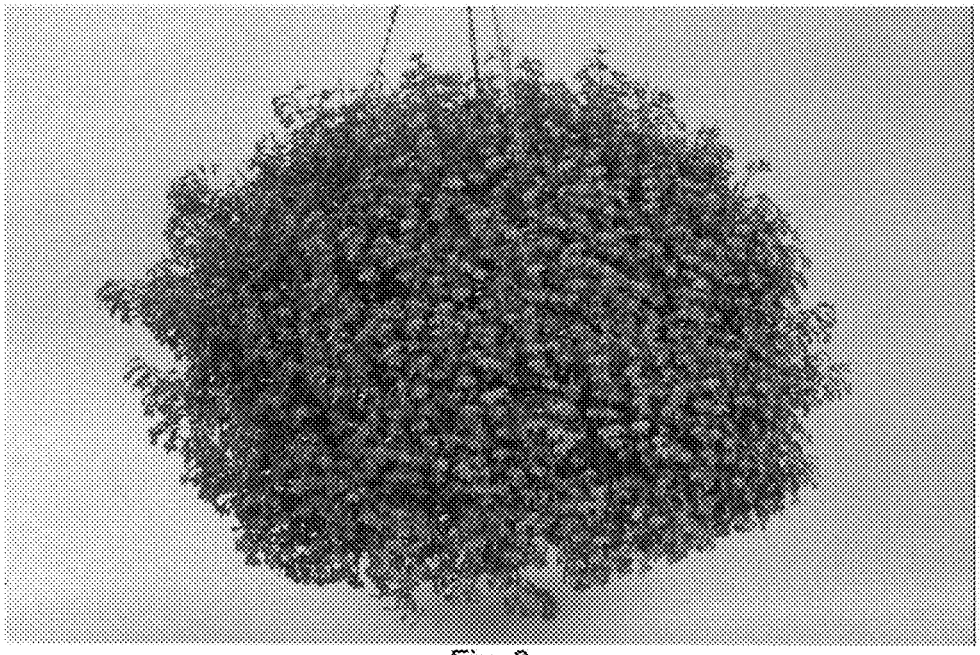
FIG. 3 shows a hanging basket holding 3 plants in full flower.

The picture was taken in mid summer when the plants were about 5 months old. The colors shown are as true as can be reasonably obtained by conventional photographic procedures.

DETAILED BOTANICAL DESCRIPTION

The measurements were taken in Hillscheid, Germany, mainly on May 5, 2007, using 15 week old plants that were growing in 12 cm pots in a greenhouse under relatively cool conditions. Culture of these plants had started in late January 2007 with planting of rooted cuttings that had been pinched once.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Lobelia* as a new and distinct variety:

1. Medium sized bright blue flowers
2. Medium green foliage
3. Freely branched, dense habit with short to medium internodes
4. Initially spreading, then over hanging and trailing

COMPARISON WITH COMMERCIAL CULTIVARS

'Tech Elebule' differs from the commercial cultivar 'Techno Blue' (registered 'Lob Bule,' U.S. Plant Pat. No. 17,250) in that 'Tech Elebule' has a slightly lighter blue flower color, different, less round, more elongate leaf shape, more velvety leaf surface with short hair, while 'Lob Bule' has glossy and glabrous foliage. Furthermore, plants of 'Tech Elebule' are somewhat taller with longer stems.

Plant:

*Growth and habit.*—Freely branched, dense habit wtih short to medium internodes.
*Form.*—Initially spreading, then over hanging and trailing.
*Height above soil.*—11–15 cm.
*Plant diameter.*—55–60 cm.
*Plant spread.*—25–30 cm (from the base of the main stem to the tips of the branches).
*Spread at the end of the summer.*—60–65 cm.
*Number of branches.*—About 80.
*Time to produce a marketable flowering plant.*—About 10 weeks for a 12 cm pot.
*Outdoor plant performance.*—Used in patio containers, in mixed container plantings, or in garden beds, full sun or partly shaded.
*Time to initiate and develop roots.*—About 24 days at 20–24° C.
*Root description.*—Fibrous and freely branching.

Stem:

*Characteristics.*—Quadrangular.
*Stem length.*—25–35 cm.
*Diameter.*—2–3 mm.
*Internode length.*—0.8–1.8 cm.
*Color.*—Deep green, RHS 137A, no anthocyanin.
*Texture.*—Short hair, hirtellous.

Foliage:

*Arrangement.*—Alternate.
*Shape.*—Oblanceolate to narrow lanceolate, on flowering stems usually very narrow, appear sessile without any distinct petiole.
*Apex.*—Acute.
*Base.*—Attenuate to acute.
*Margin.*—Crenate to weakly dentate.
*Leaf length* (*in flowering stage*).—3.2–3.5 cm.
*Leaf width.*—0.6–0.7 cm.
*Size of leaves near the base of stems or on non-flowering stems.*—Up to 5.5 cm in length, 2–2.8 cm in width.
*Color upper surface.*—Medium green, RHS 137C.
*Color lower surface.*—RHS 138A, anthocyanin may occur, RHS 187B but weak.
*Venation type.*—Pinnate.
*Venation color.*—RHS 137D on the lower side, indistinct on upper side.
*Texture.*—Both surfaces covered with very short hair, and especially along the leaf veins of lower surface and at the edges.

Inflorescence:

*Blooming habit.*—Continuous through the growing season from spring to the fall.
*Begin of flowering.*—About 10 weeks after planting of rooted cuttings in spring.
*Type of inflorescence.*—Single flowers at apical axils, with one flower per leaf node.
*Quantity of flowers per stem.*—About 4–6 open flowers, additionally buds.
*Lastingness of individual blooms on the plant.*—5–7 days.
*Fragrance.*—None.

Flower:

*Corolla type and shape.*—Single, zygomorphic; lower part tube to funnel shaped, with the petal lobes opening outwards; two small petals directed upright and 3 mainly fused petals forming the 3-lobed lower lip.
*Flower diameter, length.*—1.7–1.9 cm.
*Corolla tube length.*—0.8–0.9 cm.
*Tube width.*—0.3–0.4 cm.
*Color upper surface.*—Mainly RHS 96D, tips RHS 98A.
*Color lower surface.*—Mainly light blue, RHS 97A; the very base of the lower lip is white, RHS N155A.
*Color of tube.*—RHS 96D upper surface, lower surface RHS 97A to 97B.

Petal (lobes):

*Apex.*—Upper petals: acute; lower petals rounded to weakly mucronulate.
*Base.*—Fused.
*Margin.*—Entire.
*Texture.*—Glabrous.
*Upper lobes, length* (*from the corolla opening*).—6–7 mm.
*Upper lobes, width.*—1–2 mm.
*Lower lobe, length* (*from the corolla opening*).—9–10 mm.
*Lower lobe, width.*—6–7 mm.

Flower bud:

*Shape.*—Oblong.
*Diameter.*—0.3–0.4 cm.
*Length.*—1.0–1.2 cm.
*Color* (*at tight bud*).—RHS 97B to 98D.

Calyx:

*Form and shape.*—5 sepals in a whorl, slanting outwards.
*Sepal color.*—Outward/abaxial surface: RHS 137B. Inner surface: RHS 137B to RHS 137C.
*Length.*—6–7 mm.
*Width.*—1 mm.
*Shape of sepal.*—Ligulate.
*Apex.*—Acute, pointed.
*Base.*—Fused.
*Texture.*—Covered with short hair.

Pedicels:

*Color.*—RHS 137B.
*Length.*—2.0–2.7 cm.
*Diameter.*—0.1 cm.
*Texture.*—Covered with very short, dense hair.

Reproductive organs:

Stamens:

*Quantity.*—5.
*Filament, color.*—Blue, RHS 96D.
*Length.*—0.6 cm.
*Diameter.*—0.1 cm.
*Anther color.*—Grey, RHS 202B.
*Pollen amount.*—Little.
*Pollen color.*—RHS 8B.

Pistil:

*Quantity per flower.*—One.
*Length.*—About 1.0 cm.
*Stigma color.*—RHS N81B.
*Style color.*—RHS 145C.

Fruit and seed set: Has not been observed.

Disease/pest resistance: Disease resistance or susceptibility other than typical for the species has not been observed on this hybrid.

What is claimed is:

1. A new and distinct variety of *Lobelia* plant named 'Tech Elebule,' substantially as illustrated and described herein.

* * * * *